(12) United States Patent
Gruskin (10) Patent No.: US 11,240,977 B2
(45) Date of Patent: Feb. 8, 2022

(54) COMPACT PHOTOBIOREACTOR WITH BUILT-IN LIGHTS

(71) Applicant: Elliott A. Gruskin, Malvern, PA (US)

(72) Inventor: Elliott A. Gruskin, Malvern, PA (US)

(*) Notice: Subject to any disclaimer, the term of this patent is extended or adjusted under 35 U.S.C. 154(b) by 0 days.

(21) Appl. No.: 15/658,297

(22) Filed: Jul. 24, 2017

(65) Prior Publication Data

US 2019/0021248 A1 Jan. 24, 2019

(51) Int. Cl.

| | |
|---|---|
| *A01G 31/02* | (2006.01) |
| *A01K 61/20* | (2017.01) |
| *A01K 63/04* | (2006.01) |
| *A01K 63/06* | (2006.01) |
| *A01K 63/00* | (2017.01) |
| *C12M 1/00* | (2006.01) |
| *A01G 33/00* | (2006.01) |

(52) U.S. Cl.
CPC ............ *A01G 31/02* (2013.01); *A01G 33/00* (2013.01); *A01K 61/20* (2017.01); *A01K 63/003* (2013.01); *A01K 63/042* (2013.01); *A01K 63/045* (2013.01); *A01K 63/047* (2013.01); *A01K 63/06* (2013.01); *C12M 21/02* (2013.01); *C12M 23/38* (2013.01); *C12M 31/08* (2013.01)

(58) Field of Classification Search
CPC ........ A01H 4/001; A01G 31/06; A01G 33/00; Y02P 60/216; C12M 21/02; C12M 23/22; C12M 31/02; C12M 31/08; C12M 23/06; C12M 23/58; C12M 23/38; C12M 25/02; C12M 23/14; C12M 31/00; C12M 23/28; C12M 31/10; A01K 61/20

USPC ..................................................... 435/292.1
See application file for complete search history.

(56) References Cited

U.S. PATENT DOCUMENTS

| | | | |
|---|---|---|---|
| 4,255,383 A * | 3/1981 | Schenck ................. | A23L 3/28 210/764 |
| 4,868,123 A | 9/1989 | Berson et al. | |
| 4,952,511 A | 8/1990 | Radmer | |
| 5,104,803 A | 4/1992 | Delente | |
| 5,137,828 A | 8/1992 | Robinson et al. | |
| 5,151,347 A | 9/1992 | Delente et al. | |
| 5,160,329 A * | 11/1992 | Oxley ................. | A61B 10/007 206/438 |
| 5,162,051 A | 11/1992 | Hoeksema | |
| 6,150,166 A * | 11/2000 | Miller .................... | A01H 4/001 435/283.1 |
| 6,509,188 B1 | 1/2003 | Trösch et al. | |

(Continued)

OTHER PUBLICATIONS

Biotechnol Bioeng. Nov. 20, 1994;44(10):1161-7. High-density algal photobioreactors using light-emitting diodes. Lee CG, Palsson Bø.

(Continued)

*Primary Examiner* — Peter M Poon
*Assistant Examiner* — Jeffrey R Larsen
(74) *Attorney, Agent, or Firm* — Farber LLC (57) ABSTRACT

A photobioreactor device for growing photosynthetic organisms, organisms that feed on photosynthetic organisms and hydroponics is disclosed. The device may include a lighting system integrated around the circumference of the device. In embodiments, a cap configured to seal the container has ports configured to permit passage of fluid out of or into a container without removing the cap. In some embodiments, organisms are grown in a disposable bag secured between the cap and the container.

29 Claims, 9 Drawing Sheets

(56) References Cited

U.S. PATENT DOCUMENTS

| | | | |
|---|---|---|---|
| 6,571,735 B1* | 6/2003 | Wilkinson | C12M 21/02 |
| | | | 119/215 |
| 6,602,703 B2 | 8/2003 | Dutil | |
| 7,618,813 B2 | 11/2009 | Lee et al. | |
| 7,824,904 B1 | 11/2010 | Dimanshteyn | |
| 7,997,025 B1 | 8/2011 | Masse | |
| 8,003,370 B2 | 8/2011 | Maltezos et al. | |
| 8,110,395 B2 | 2/2012 | Lewnard et al. | |
| D661,644 S | 6/2012 | Heidtmann | |
| 8,198,076 B2 | 6/2012 | Hu et al. | |
| 8,241,895 B2 | 8/2012 | Hu et al. | |
| 8,318,478 B2 | 11/2012 | Dahle | |
| 8,341,877 B2 | 1/2013 | Licamete et al. | |
| D679,965 S | 4/2013 | Licamele | |
| 8,409,845 B2 | 4/2013 | Trent et al. | |
| D682,637 S | 5/2013 | Licamele | |
| 8,470,540 B2 | 6/2013 | Green et al. | |
| 8,470,584 B2 | 6/2013 | Bayless et al. | |
| 8,479,441 B2 | 7/2013 | Williamson et al. | |
| 8,569,050 B1 | 10/2013 | Ericsson | |
| 8,586,344 B2 | 11/2013 | Mueller-Rees et al. | |
| 8,642,326 B1 | 2/2014 | Schaefer et al. | |
| 8,658,420 B2 | 2/2014 | Gomey et al. | |
| 8,658,421 B2 | 2/2014 | Kim et al. | |
| 8,722,396 B2 | 5/2014 | Kassebaum et al. | |
| 8,765,460 B2 | 7/2014 | Nordvik et al. | |
| 8,809,041 B2 | 8/2014 | Woerlee et al. | |
| 8,822,199 B2 | 9/2014 | Muller-Feuga et al. | |
| 8,852,924 B2 | 10/2014 | Maranhao | |
| 8,877,487 B2 | 11/2014 | Slagel | |
| 8,895,279 B2 | 11/2014 | Burke | |
| 8,940,518 B2 | 1/2015 | Meiser et al. | |
| 8,945,916 B2 | 2/2015 | Chou | |
| 8,955,249 B2 | 2/2015 | Veres et al. | |
| 8,986,985 B2 | 3/2015 | Levin | |
| 9,005,918 B2 | 4/2015 | Dvorak et al. | |
| 9,040,283 B2 | 5/2015 | Muller-Feuga | |
| 9,045,724 B2 | 6/2015 | Roux Dit Buisson | |
| 9,102,923 B2 | 8/2015 | Meiser et al. | |
| 9,115,008 B2 | 8/2015 | Farrish | |
| 9,181,520 B2 | 11/2015 | Lee et al. | |
| 9,222,065 B2 | 12/2015 | Lee et al. | |
| 9,284,519 B2 | 3/2016 | Aikens et al. | |
| 9,290,733 B2 | 3/2016 | Muller-Feuga | |
| 9,295,206 B2 | 3/2016 | Jovine | |
| 9,329,131 B2 | 5/2016 | Dodge et al. | |
| 9,347,030 B2 | 5/2016 | Fiorentino | |
| 9,376,656 B2 | 6/2016 | Bartilson | |
| 9,382,508 B2 | 7/2016 | Schuessler et al. | |
| 9,445,551 B2 | 9/2016 | Chapman et al. | |
| 9,453,193 B2 | 9/2016 | Babbitt et al. | |
| 9,464,303 B2 | 10/2016 | Burke | |
| 9,469,832 B2 | 10/2016 | Mena Mas | |
| 9,518,248 B2 | 12/2016 | Erickson et al. | |
| 9,523,069 B2 | 12/2016 | Jeong et al. | |
| 9,523,070 B2 | 12/2016 | Erickson et al. | |
| 9,534,194 B2 | 1/2017 | Vellinga | |
| 9,637,714 B2 | 5/2017 | Willson et al. | |
| 9,644,176 B2 | 5/2017 | Henderson | |
| 9,688,950 B2* | 6/2017 | Roulston | C12M 21/02 |
| 9,708,207 B2 | 7/2017 | Farrish | |
| 2002/0102719 A1* | 8/2002 | Adelberg | A01G 9/026 |
| | | | 435/292.1 |
| 2009/0313894 A1* | 12/2009 | Bieber | A01G 31/00 |
| | | | 47/62 R |
| 2010/0105125 A1* | 4/2010 | Haley, III | C12M 21/02 |
| | | | 435/257.1 |
| 2011/0154985 A1* | 6/2011 | Mittelmark | A01G 27/00 |
| | | | 95/1 |
| 2012/0107792 A1* | 5/2012 | Babbitt | C12M 21/02 |
| | | | 435/3 |
| 2016/0130542 A1* | 5/2016 | Wilson | A01K 63/06 |
| | | | 435/257.1 |
| 2017/0362561 A1* | 12/2017 | Chung | C12M 21/02 |

OTHER PUBLICATIONS

Appl Microbiol Biotechnot. Mar. 2011. 89(5):1275-88. doi: 10.1007/s00253-010-3047-8. Epub Dec. 23, 2010. Light requirements in microalgal photobioreactors: an overview of biophotonic aspects, Carvalho AP, Silva SO, Baptsta JM, Malcata FX.

Water Sci Technol. 2013;67(11)2543-8, doi: 10.2166/wst.201.3.128. A novel optical panel photobioreactor for cultivation of microalgae. Choi HJ, Lee JM, Lee SM.

Trends Biotechnol Aug. 2014. 32(8):422-30. doi: 10.1016/j.tibtech.2014.06.001. Epub Jul. 8, 2014. Light emitting diodes (LEDs) applied to microalgal production. Schulze PS. Barreina LA, Pereira HG, Persies JA, Varela JC.

World J Microbiol Biotechinol. Sep. 2015, 31(9):1409-17 doi: 10.1007/611274-015-1892-4. Epub Jun. 20, 2015 18. A mint review: photobioreactors for large scale algal cultivation. Gupta PL. Lee SM, Chai H].

Appl Microbial Biotechnot. Feb. 2016;100(3) 1077-88 doi: 10.1007/s00253-015-7144-6. Epub Nov. 21, 2015 Application of light-emitting diodes (LEDs) in cultivation of phototrophic microalgae: current state 25 and perspectives. Glemser M, Heining M. Schmidt J, Becker A, Garbe D, Buchholz R, Brück T.

Bioresour Technol. Sep. 2016;2 16:845-55 doi: 10.1016/j.biortech.2016.06.027. Epub Jun. 11, 2016. Pilotscale bubble column photobioreactor culture of a marine dinoflagellate microalga illuminated with light emission diodes. López-Rosales L. Garcia-Camacho F, Sánchez-Mirón A, Martin Beato E, Chisti Y, Molina Grima E.

* cited by examiner

Copepod Set-Up

Figure 15

Macroalgae Set-Up

COMPACT PHOTOBIOREACTOR WITH BUILT-IN LIGHTS

CROSS REFERENCES TO RELATED APPLICATIONS

This application claims priority to, and the benefit of Provisional Patent Application 62/366,283 filed on Jul. 25, 2016.

TECHNICAL FIELD

This disclosure relates to the general field of photobioreactors, and has certain specific applications for growing photosynthetic organisms, organisms that feed on photosynthetic organisms and hydroponics.

BACKGROUND

Photobioreactors are used to cultivate photosynthetic organisms. These organisms use light to generate organic compounds from carbon dioxide to provide energy and other substances to maintain growth, reproduction and survival. Examples of photosynthetic organisms include plants, macro and microalgae and certain types of bacteria. Photobioreactors can also be used to cultivate organisms such as copepods and brine shrimp that feed on photosynthetic organisms cultivated in a photobioreactor. Most photobioreactors are designed to cultivate organisms in the presence of sunlight. They are generally large units able to cultivate significant volumes of organisms. Examples of these photobioreactors include Tubular, Christmas Tree, Plate, Horizontal, Foil and Porous Substrate Photobioreactors. There are also smaller photobioreactors used in laboratory settings that are based on microbiological fermentation systems. These laboratory-based systems generally require other supporting laboratory equipment such as autoclaves, power supplies, computer controllers, pH meters and sterile tissue culture hoods. Finally, hobbyists and small commercial entities use improvised photobioreactors that generally consist of containers fitted with aeration tubes that are placed in front of fluorescent lights.

SUMMARY

The present invention is designed for hobbyists or small commercial entities that intend to run a photobioreactor indoors without sunlight and do not have access to supporting laboratory equipment. Current photobioreactors for these users generally consist of clear culture vessels into which is placed an aeration tube. The culture vessels are placed in front of a bank of fluorescent lights. There have been disclosures of culture systems with built in lights. Typically, these lights are housed in a tube that extends into the center of the culture vessel. These systems must be thoroughly cleaned after each culture to prevent contamination. The process is unreliable and time consuming.

The present photobioreactors have several advantages over current photobioreactors. Since the light source is integrated into the culture vessel there is no need for external light sources and so a lot less space is required to culture the same volume of photosynthetic organisms. In addition, because the light source in the current photobioreactors is positioned around the circumference of the culture vessel the light path that illuminates the culture is reduced compared to a single light source external to the culture vessel or designed in a chamber within the culture vessel, as is the case with other culture containers. As a result, the culture is more effectively and uniformly illuminated. Another advantage is the use of a plastic bag liner as the primary culture contacting surface. Disposable plastic bags can be obtained that are sufficiently clean without additional sterilization to allow their direct use without the risk of culture contamination. The bag is then disposed of after the culture is grown and this dramatically simplifies the culture process and obviates the need to extensively clean the culture vessel between cultures. An additional advantage to the current photobioreactors is the cap system. Preferably the cap is made of rubber to allow repeated cleaning and sterilization with rubbing alcohol or household bleach. Furthermore, the cap has several bulkheads with quick connect fittings such that aeration and dosing tubes can be easily changed between cultures. In addition, the cap has a circumferential clamp with a thumbscrew so that is can be easily placed over the primary container and tightened in place, thus trapping the plastic bag liner between the primary culture vessel and the cap. Since the cap creates an airtight fit, the aeration tube produces positive pressure within the culture container. Furthermore, the air admitted into the culture container can be passed through a sub-micron, in-line air filter. The combination of sub-micron filtered air and positive pressure in the culture container decreases the likelihood of contamination of the culture compared to current methods.

BRIEF DESCRIPTION OF THE DRAWINGS

Various embodiments of the invention are disclosed in the following detailed description and accompanying drawings.

DETAILED DESCRIPTION

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

Figure 1:
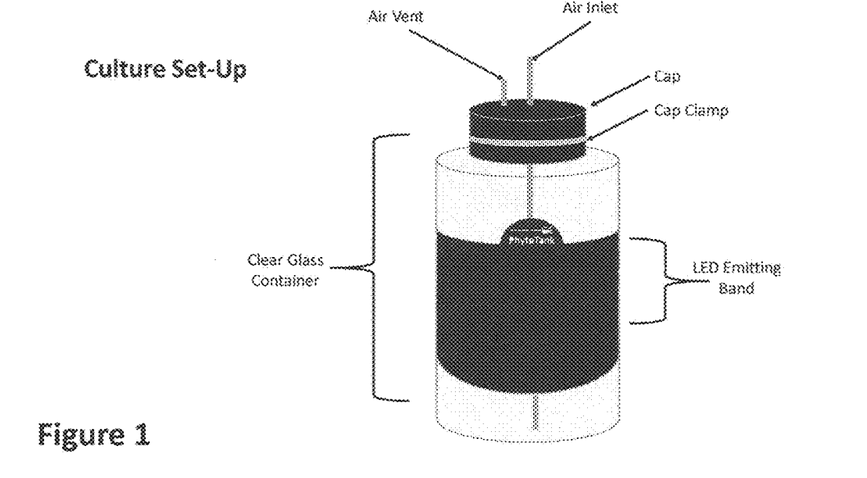
FIG. 1 illustrates the compact photobioreactor in the culture configuration.
Figure 2:
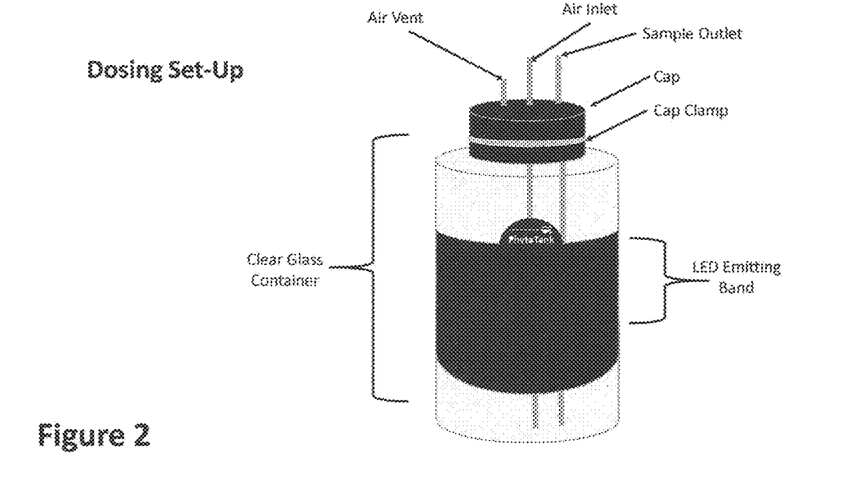
FIG. 2 illustrates the compact photobioreactor in the dosing configuration
Figure 3:
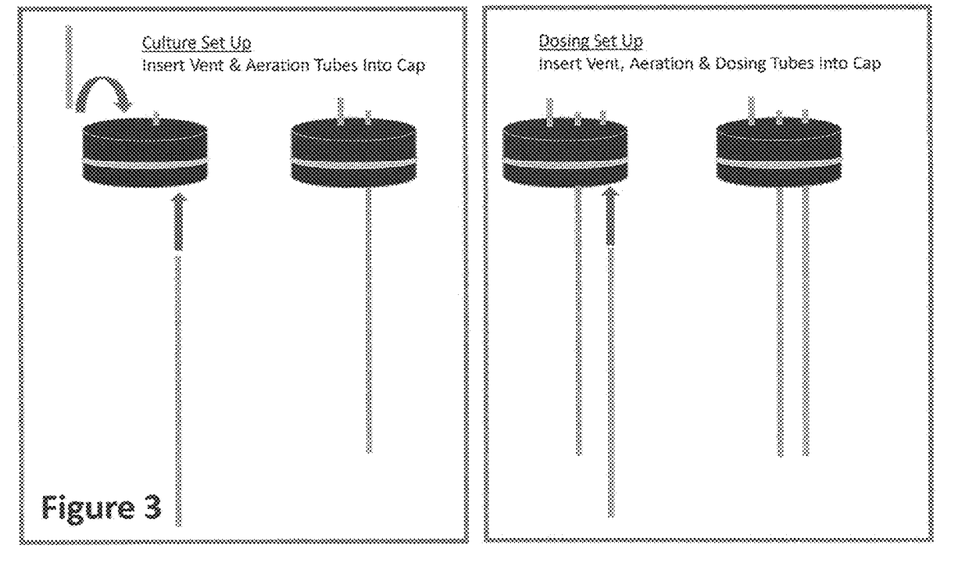
FIG. 3 illustrates the configuration of the cap for both a culture and dosing configuration.

In one embodiment of the invention, the compact photobioreactor is used to grow a culture of phytoplankton. The compact photobioreactor can be configured to grow a culture of phytoplankton (FIG. 1) and it can also be configured to allow portions of the phytoplankton to be sampled from the compact photobioreactor (FIG. 2). The compact photobioreactor phytoplankton culture system consists of a plastic bag liner placed inside a clear glass or plastic contained that has a central band of LED lights affixed to the outside of the circumference of the system (FIG. 3). The Phytoplankton culture takes place in a plastic bag that is placed inside the clear glass or plastic container. The plastic bag is the primary container for the culture. The clear glass or plastic container is a secondary container that constrains the plastic bag which conforms to the size and shape of the secondary container. The integrated LED lighting system is a central band on the outside of the secondary clear glass or plastic container and consists of LED light strips attached to the outside of the clear glass or plastic culture container such that the light is transmitted into the container. The next layer is a reflective coating, for example a layer of foil that acts as a light reflector. The final layer is an opaque covering over the LED system. The opaque outer band protects the LED lighting system, provides a sturdy surface to grip the culture system and also provides a durable protective surface that allows multiple culture systems to be placed next to each other without the risk of cracking or damaging the secondary culture container.

Figure 4:
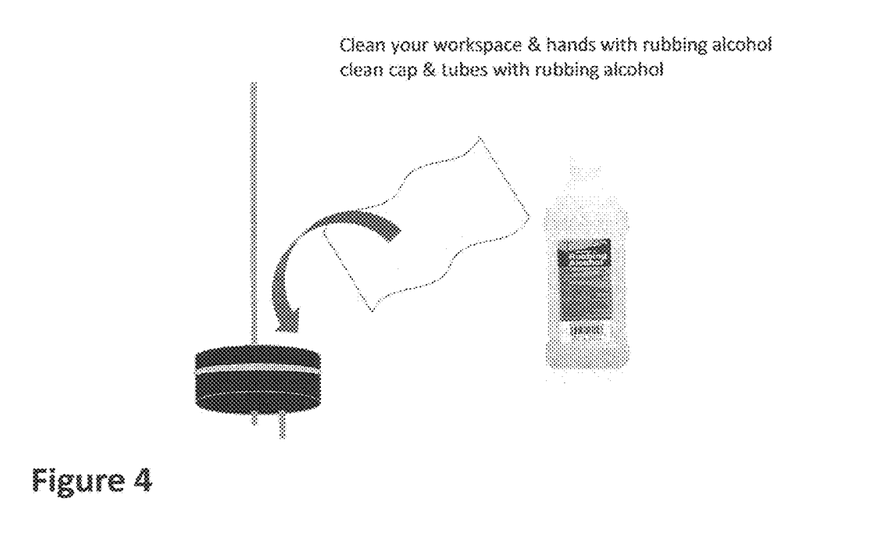
FIG. 4 illustrates the method for disinfecting the cap assembly with rubbing alcohol.
Figure 5:
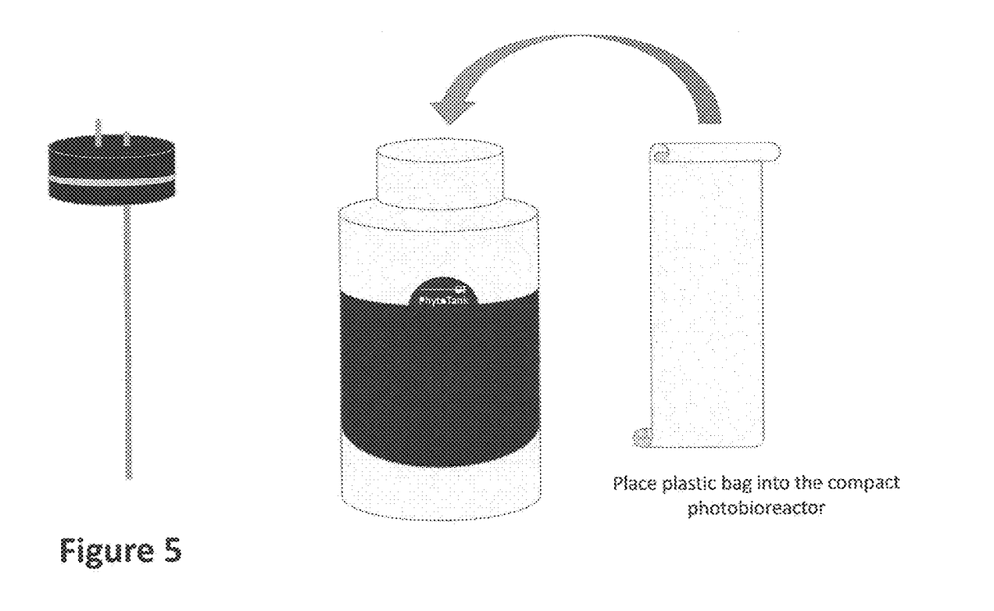
FIG. 5 illustrates the method for placing the disposable culture bag into the compact photobioreactor.
Figure 6:
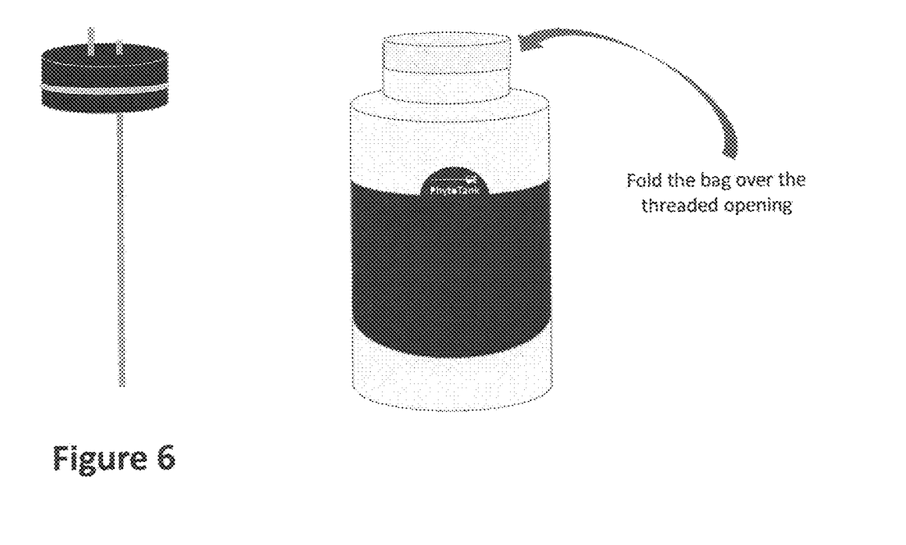
FIG. 6 illustrates the method for folding the plastic bag over the opening of the compact photobioreactor.
Figure 7:
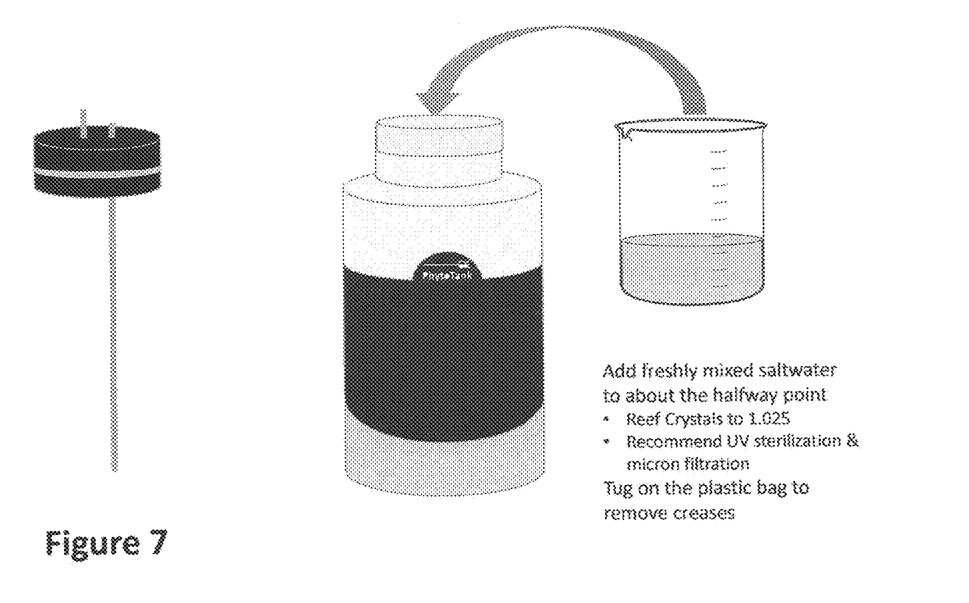
FIG. 7 illustrates the addition of salt water to the compact photobioreactor.
Figure 8:
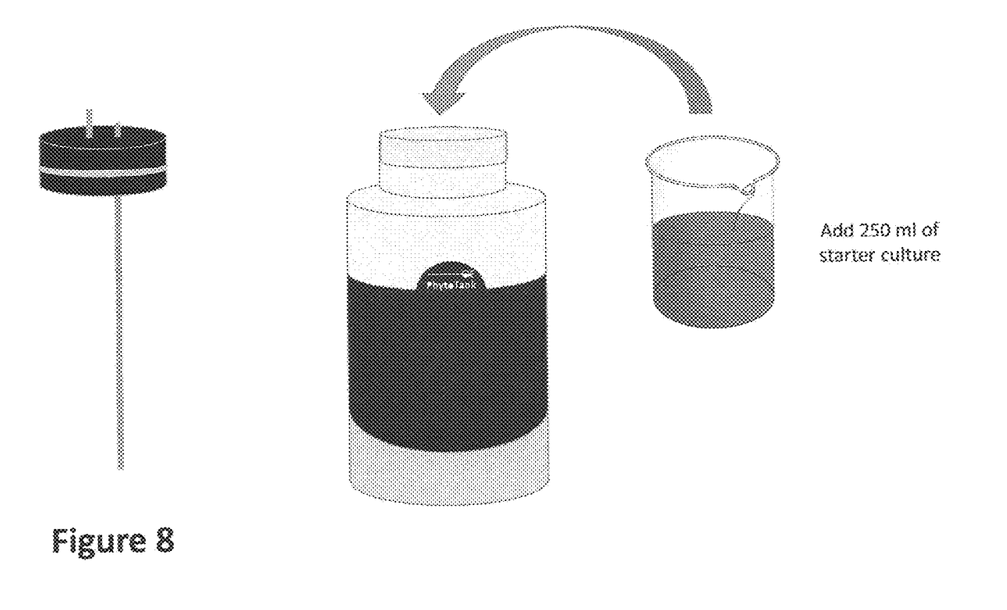
FIG. 8 illustrates the addition of a starter culture to the compact photobioreactor
Figure 9:
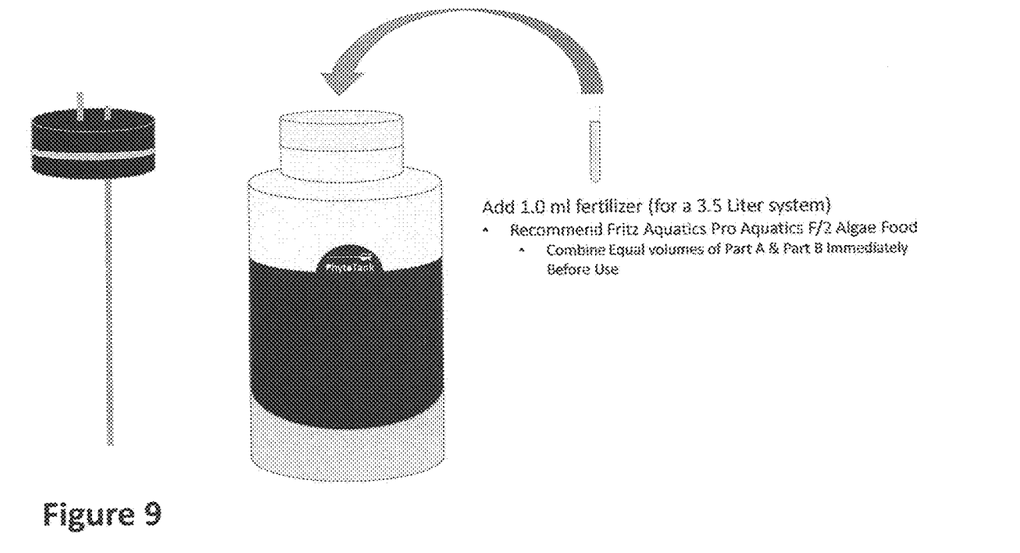
FIG. 9 illustrates the addition of fertilizer to the compact photobioreactor.
Figure 10:
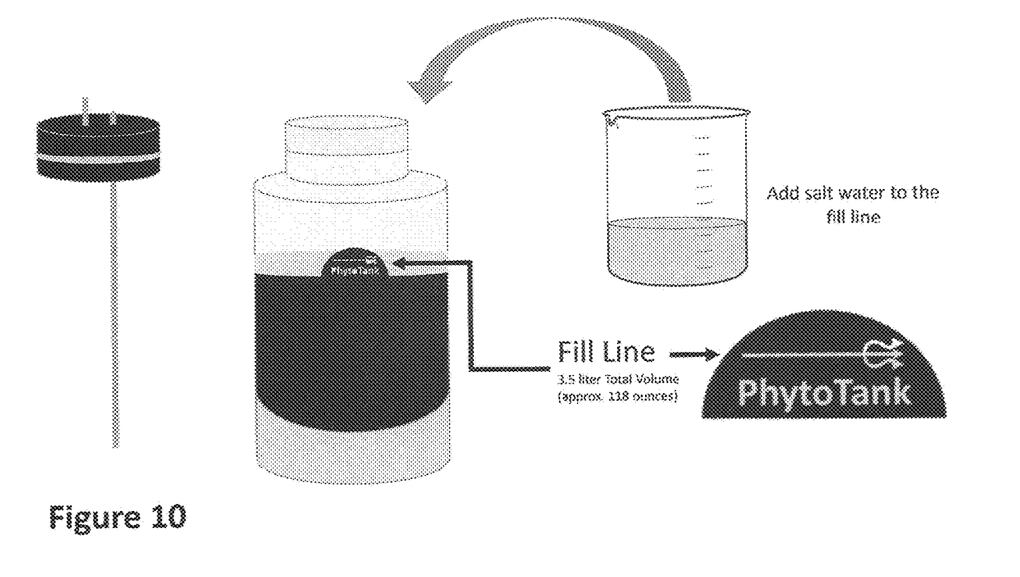
FIG. 10 illustrates the addition of salt water to the fill line of the compact photobioreactor.
Figure 11:
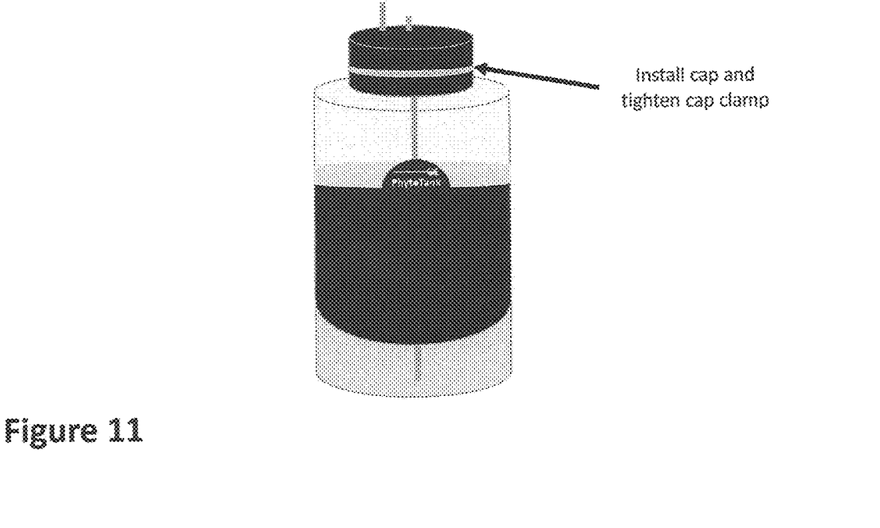
FIG. 11 illustrates the installation of the cap to the compact photobioreactor.
Figure 12:
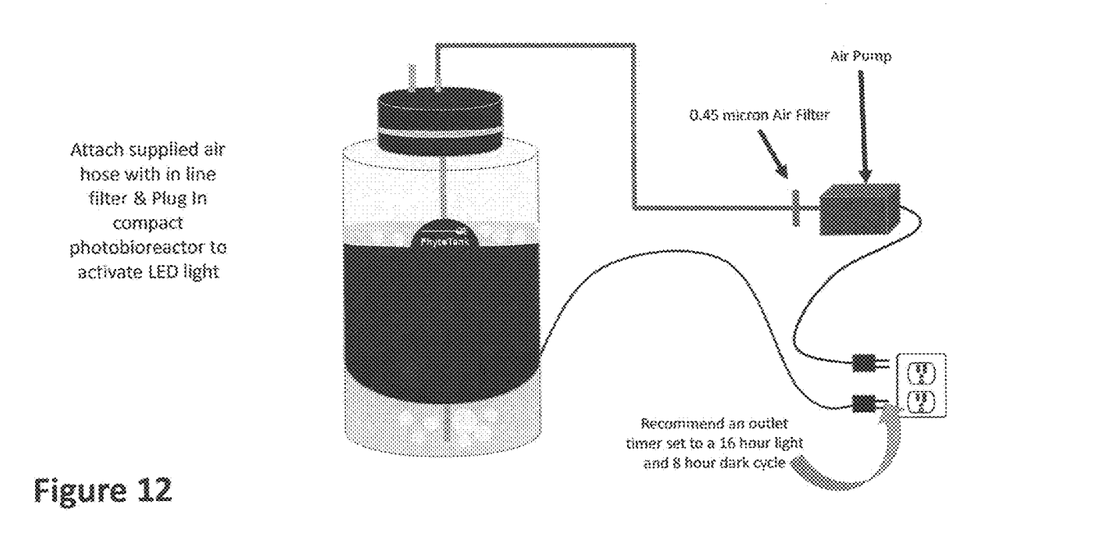
FIG. 12 illustrates the attachment of the air supply and light power supply to the compact photobioreactor.
Figure 13:
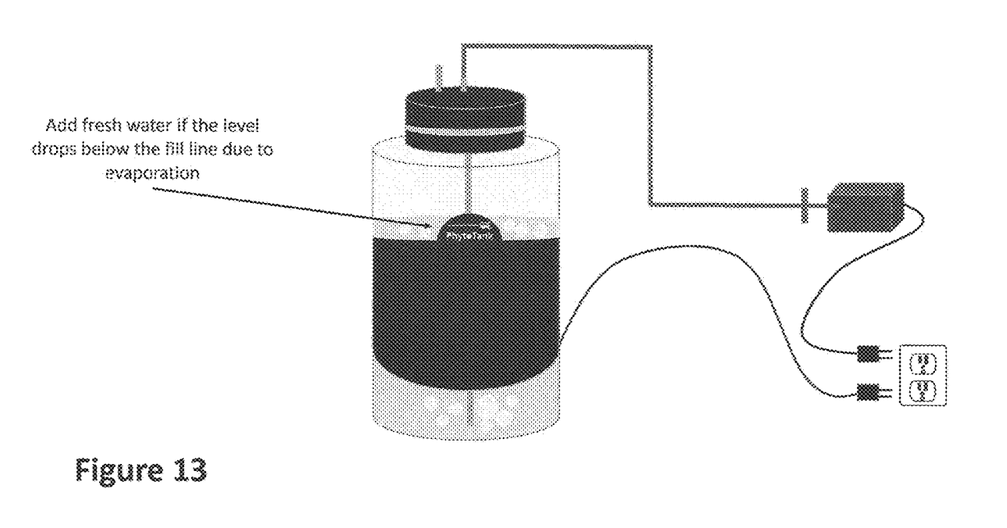
FIG. 13 illustrates the maintenance of the correct water level in the compact photobioreactor.
Figure 14:
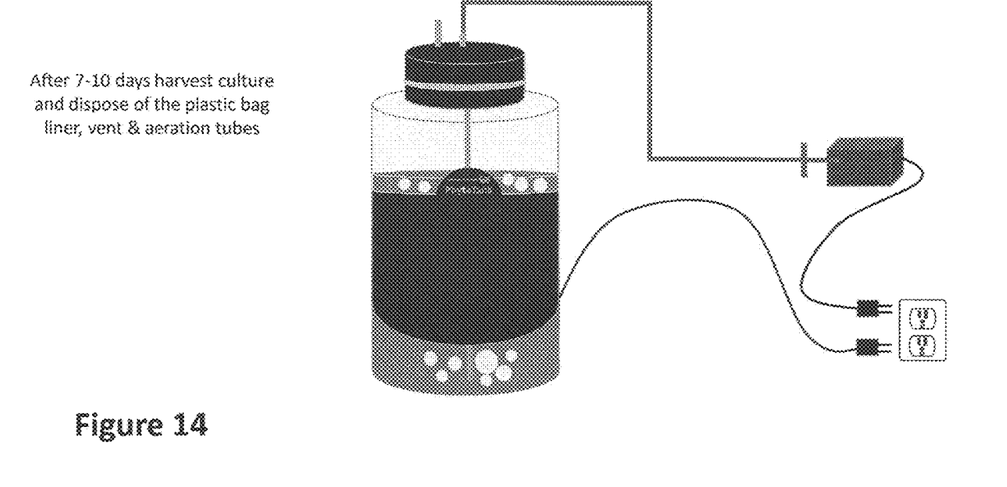
FIG. 14 illustrates the completion of a culture process.

The first step to use the Phytoplankton culture system is to insert plastic tubes into the cap's quick connect bulkhead fittings for the air vent, aeration and dosing (FIG. 3). The work surface, user's hands and the assembled cap is cleaned with rubbing alcohol to prevent contamination (FIG. 4). The clear plastic bag is placed inside the secondary container and the opening of the bag is folded over the opening of the secondary container (FIG. 5). Freshly prepared salt water (specific gravity 1.025) is then poured into the plastic bag to about the half way point (FIG. 7). A started culture volume of at least one tenth of the final culture volume is added to the system (FIG. 8) and then 1 ml of an appropriate algae fertilizer (such as Fritz Aquatics Pro Aquatics F/2 Algae Food) is added per gallon of final culture volume (FIG. 9). Additional salt water is added to bring the final volume to the Fill Line marked on the secondary container (FIG. 10). The cap is then placed on the secondary container trapping the plastic bag between the cap and the secondary container and the cap clamp is tightened (FIG. 11). The final step is to attach an airline with a sub-micron in-line air filter to the aeration port and then plug the LED light into a timed outlet to provide a 16-hour light, 8-hour dark cycle (FIG. 12). After 7-14 days, the phytoplankton culture is ready to be harvested. To grow another culture, the plastic bag air vent, aeration and dosing tubes are replaced and the set up sequence is repeated.

Figure 15:
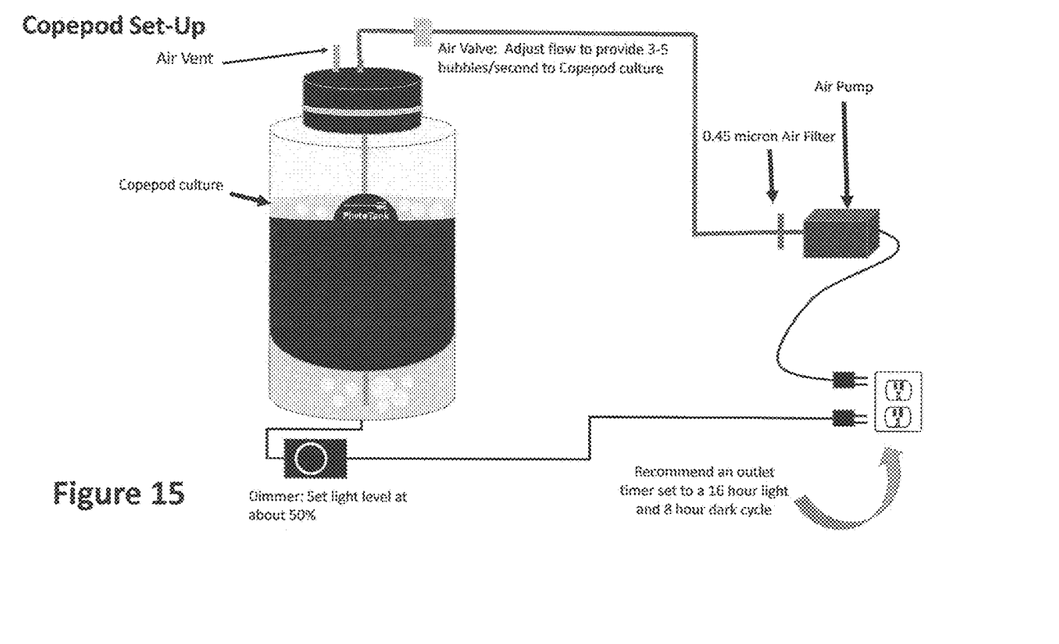
FIG. 15 illustrates the setup of the compact photobioreactor for the culture of organisms like copepods and brine shrimp that consume phytoplankton for survival and growth.

In a second embodiment the compact photobioreactor is used to grow and maintain a culture of an organism that feeds upon phytoplankton. Examples include copepods and brine shrimp. In this embodiment, the photobioreactor is prepared as previously described. However, instead of adding a small volume of a phytoplankton starter culture, a large volume of dense phytoplankton is added to the container. Also added to the container is a population of copepods or brine shrimp that will feed on the phytoplankton to grow and reproduce. Organisms such as tisbe copepods are benthic and prefer a substrate to grow on. For these benthic organisms, substrates can be placed into the container to support growth. These substrates can be naturally derived such as small rocks or shells, or they can be synthetic such as ceramics, meshes or sponges. In one method, a small air lift filter can be attached to the aeration tube and fitted with a nylon mesh. In addition, some organisms require gentile aeration. To provide gentle aeration the airline can be fitted with a valve to control the air flow into the container. Additionally, some organisms require lower light levels for optimum growth and survival. In these cases, a dimmer switch can be used between the power supply and the compact photobioreactor to adjust the light level as appropriate. The diagram in FIG. 15 shows an illustrative configuration of the compact photobioreactor for this application. After an appropriate period of time, for example after a majority of the phytoplankton has been consumed and the culture is no longer the same starting color of the dense phytoplankton, the copepods and brine shrimp are recovered. One method to recover the copepods or brine shrimp is to pour the culture contents through a 50-100 micron sieve that allows the culture solution and residual phytoplankton to pass through, but traps the copepods or brine shrimp. These organisms can then be recovered from the sieve by inverting it and pouring fresh salt water through it into an appropriate container thus collecting the organisms in a new volume of water. The photobioreactor can be prepared for another culture in same way as described above. The plastic bag liner and aeration tubes can be disposed of and then new materials are used to restart the culture.

Figure 16:
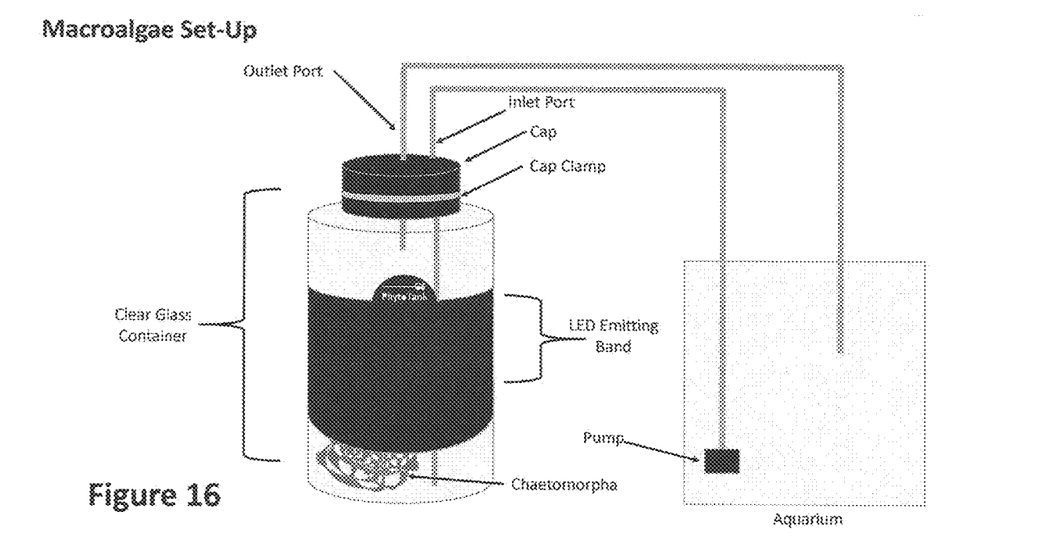
FIG. 16 illustrates the configuration of the compact photobioreactor to grow and maintain macroalgae while circulating aquarium water through the compact photobioreactor.

In another embodiment, the compact photobioreactor can be used to grow and maintain macroalgae such as chaetomorpha. Marine aquariums benefit from low phosphate and nitrate levels. One method to maintain low levels is to expose the aquarium water to macroalgae such as chaetomorpha. This is often accomplished by placing macroalgae in a sump or refugium and illuminating it with light. The macroalgae consumes phosphate and nitrate to grow thus removing those chemicals from the aquarium water. When a large amount of macroalgae accumulates, some of it can be removed thus exporting phosphate and nitrate from the environment. The remainder can be left in the sump or refugium to repeat the cycle. The present disclosure offers an alternative and advantageous method. The compact photobioreactor is constructed as described above, however in this embodiment, the cap is configured differently. It is equipped with two bulkheads, one for the introduction of aquarium water (inlet port), and a second for the return of aquarium water (outlet port) (FIG. 16). A submersible pump is placed in the aquarium, sump or refugium and the discharge tube for this pump is connected to the inlet port of the compact photobioreactor. Macroalgae is placed into the compact photobioreactor and the cap is secured in place with the cap clamp. The outlet port of the compact photobioreactor is attached to a tube that terminates in the aquarium. In this configuration, water is pumped from the aquarium into the inlet port of the compact photobioreactor where it comes in contact with the macroalgae. It is then returned to the aquarium through the outlet port. The built-in lights on the compact photobioreactor provide the light required for the growth and survival of the macroalgae. Consequently, in this embodiment, aquarium water is continuously cycled through the compact photobioreactor where it comes in contact with macroalgae. The macroalgae is illuminated inside the compact photobioreactor and consumes phosphate and nitrate from the aquarium water. After the macroalgae grows to the point where it is densely packed within the compact photobioreactor the pump is turned off and the cap removed. A portion of the macroalgae can then be removed and discarded. The remainder is left in the compact photobioreactor, the lid is secured using the clamp and then the pump turned back on to resume operation.

Figure 17:
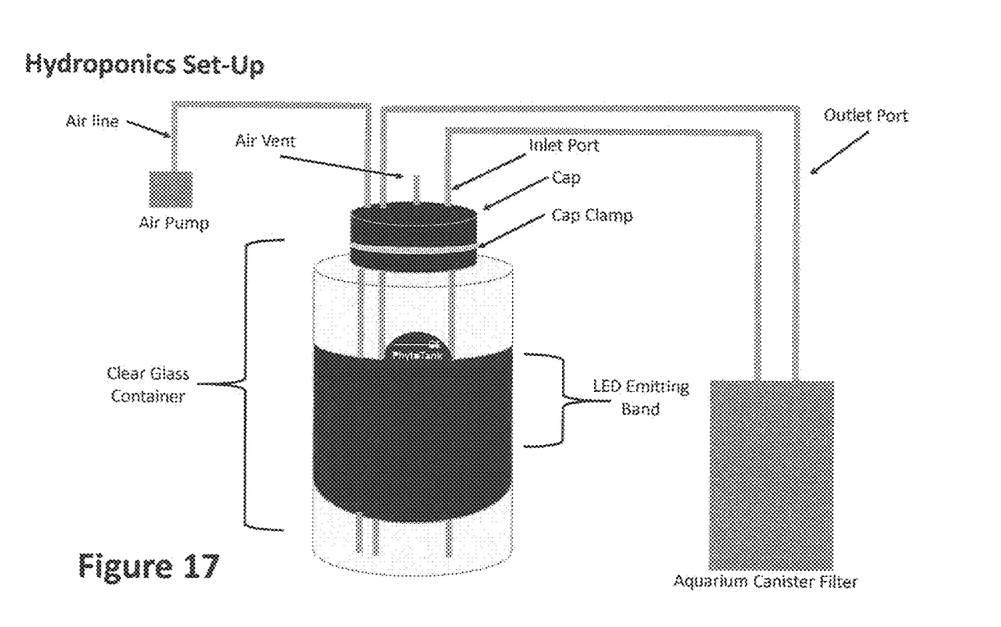
FIG. 17 illustrates the configuration of the compact photobioreactor to grow and maintain plants.

In another embodiment, the compact photobioreactor can be used to grow and maintain a plant as a hydroponics system. In this embodiment, a plant in a mesh pot is placed inside the compact photobioreactor with a volume of hydroponics medium such that the mesh pot is submerged but the rest of the plant is above the water level. In this configuration, the cap is equipped with a water inlet and outlet, both of which are connected to tubes that extend from the cap into the container and terminate below the level of the hydroponics medium (FIG. 17). The inlet and outlet tubes are connected to a standard aquarium canister filter such that the water is syphoned out of the compact photobioreactor, passed through the aquarium canister filter's filtration medium and pumped back into the compact photobioreactor through the inlet port. In some instances, it is desirable to limit the growth of nuisance microorganisms by placing a UV light in the external water circuit to sterilize the hydroponics media. In some instances, aquarium canister filters have built-in UV lights to for this purpose. In this embodiment, the aeration tube is used to aerate the hydroponics medium.

The disclosed embodiments are illustrative, not restrictive. While specific configurations of the compact photobioreactor have been described, it is understood that the present invention can be applied to the growth and maintenance of a wide variety of photosynthetic organisms. There are many alternative ways of implementing the invention.

What is claimed is:

1. A compact photobioreactor comprising:
   a transparent container having an inner surface and an outer surface;
   a lighting system around an outer circumference on the outer surface of the container;
   a reflective coating situated over and around the lighting system such that the lighting system is positioned between the outer surface of the container and the reflective coating;
   a protective opaque band supported on the outer surface of the container and positioned around a central portion of the outer circumference of the container, the protective opaque band covering the lighting system and the reflective coating such that the reflective coating is positioned between the lighting system and the opaque band, the opaque band having a height that is less than the height of the container; and
   a cap configured to seal the container, the cap having at least one port configured to permit passage of fluid out of or into the container without removing the cap.

2. The photobioreactor of claim 1, wherein the cap is made from a material selected from the group consisting of rubber, vinyl, silicone, and plastic.

3. The photobioreactor of claim 1, further comprising a circumferential clamp configured to secure the cap to the container.

4. The photobioreactor of claim 1, wherein the protective opaque band is made from a material selected from the group consisting of rubber, vinyl, silicone, and plastic.

5. The photobioreactor of claim 1, wherein the protective opaque band is textured.

6. The photobioreactor of claim 1, further comprising a bag positioned within and everted over a top edge of the container.

7. The photobioreactor of claim 6, wherein the bag is secured between the container and the cap.

8. The photobioreactor of claim 7, wherein the plurality of ports are each configured to allow for attachment of a tube configured to allow fluids to be admitted to, or removed from, the bag without having to remove the cap.

9. The photobioreactor of claim 8, further including a first tube configured to introduce water from an aquarium into the bag and a second tube configured to return water to the aquarium from the bag.

10. The photobioreactor of claim 9, wherein the first tube is configured to add hydroponic medium to the bag and the second tube is configured to remove hydroponic medium from the bag.

11. The photobioreactor of claim 1, wherein at least one of the plurality of ports is attached to a pump, the pump configured to introduce or remove fluid into or out of the container without having to remove the cap.

12. The photobioreactor of claim 11, further including an inline, sub-micron air filter attached to at least one of the plurality of ports.

13. The photobioreactor of claim 1 wherein the lighting system includes LED lights.

14. The photobioreactor of claim 13, further comprising a dimmer switch connected to the lighting system, the dimmer switch configured to control the intensity of the lighting system.

15. The photobioreactor of claim 1, wherein the at least one port includes a bulkhead to allow for attachment of a tube.

16. The photobioreactor of claim 1, further comprising an external canister filter.

17. The photobioreactor of claim 16, wherein the external canister filter further comprises a UV sterilizer.

18. A method for using a photobioreactor comprising:
   positioning a clear bag within a transparent container having an inner surface and an outer surface, and folding an edge of the bag over an opening of the container, the container including a lighting system around an outer circumference on the outer surface of the container, a reflective coating situated over and around the lighting system such that the lighting system is positioned between the outer surface of the container and the reflective coating, and a protective opaque band positioned on the outer surface of the container and positioned around a central portion of the outer circumference of the container, the protective opaque band covering the lighting system and the reflective coating such that the reflective coating is positioned between the lighting system and the opaque band, the opaque band having a height that is less than the height of the container;

adding a composition to the bag;

securing a cap over the opening of the container, trapping a portion of the bag between the cap and the container, the cap including at least one port configured to permit passage of fluid out of or into the bag without having to remove the cap;

introducing fluid into the bag using a tube positioned through the at least one port, the tube attached to a pump; and activating the lighting system.

19. The method as in claim 18, wherein adding a composition to the bag includes adding salt water, fertilizer, and phytoplankton cultures.

20. The method as in claim 18, wherein adding a composition to the bag includes adding zooplankton.

21. The method as in claim 18, wherein adding a composition to the bag includes adding a culture of organisms that consume phytoplankton.

22. The method as in claim 18, further comprising adding a substrate into the bag.

23. The method as in claim 22, wherein the substrate is a natural material.

24. The method as in claim 22, wherein the substrate is a synthetic material.

25. The method as in claim 24, wherein the substrate is part of a submersible air filter.

26. The method as in claim 18, wherein adding a composition to the bag includes adding chaetomorpha to the bag, the method further comprising removing phosphates and nitrates from aquarium water.

27. The method of claim 18, wherein introducing fluid into the bag includes introducing hydroponic media into the bag, the method further comprising placing plants in the bag.

28. The method of claim 27, further comprising aerating the hydroponic media using a second tube connected to an external air pump that is passed through the cap using a bulkhead.

29. A photobioreactor comprising:

a transparent container having an inner surface and an outer surface;

a lighting system around an outer circumference on the outer surface of the container;

a reflective coating situated over and around the lighting system such that the lighting system is positioned between the outer surface of the container and the reflective coating;

a protective opaque band supported on the outer surface of the container, the protective opaque band positioned around a central portion of the outer circumference of the container such that the protective opaque band defines a gripping surface for gripping the container, the protective opaque band covering the lighting system and at least a portion of the reflective coating such that at least a portion of the reflective coating is positioned between the lighting system and the opaque band, the opaque band having a height that is less than the height of the container; and a cap configured to seal the container, the cap having at least one port configured to permit passage of fluid out of or into the container without removing the cap.

* * * * *